United States Patent [19]

Shibata et al.

[11] 4,247,696
[45] Jan. 27, 1981

[54] PROCESS FOR PREPARING GAMMA PHASE QUINACRIDONE

[75] Inventors: Katusya Shibata, Shinnanyo; Motohiro Hamada, Tokuyama; Eiji Iwamoto, Shinnanyo, all of Japan

[73] Assignee: Toyo Soda Manufacturing Co., Ltd., Nanyo, Japan

[21] Appl. No.: 24,368

[22] Filed: Mar. 27, 1979

[30] Foreign Application Priority Data

Apr. 1, 1978 [JP] Japan .................................. 53-37467
Apr. 5, 1978 [JP] Japan .................................. 53-39261

[51] Int. Cl.$^3$ ............................................. C09B 48/00
[52] U.S. Cl. .................................. 546/49; 106/288 Q
[58] Field of Search ...................... 546/49; 106/288 Q

[56] References Cited

U.S. PATENT DOCUMENTS

| | | | |
|---|---|---|---|
| 3,201,402 | 8/1965 | Bohler et al. | 546/56 |
| 3,738,988 | 6/1973 | Jackson | 546/49 |
| 4,094,699 | 6/1978 | Fitzgerald | 546/49 X |

FOREIGN PATENT DOCUMENTS

| | | | |
|---|---|---|---|
| 44-21856 | 9/1969 | Japan | 546/49 |
| 948487 | 2/1964 | United Kingdom | 546/49 |

*Primary Examiner*—Donald G. Daus
*Assistant Examiner*—Diana G. Rivers
*Attorney, Agent, or Firm*—Cushman, Darby & Cushman

[57] ABSTRACT

Finely divided gamma crystal phase quinacridone pigments are prepared by a process wherein a crude quinacridone of an arbitrary crystal phase is dissolved in dimethyl sulfoxide in the presence of a caustic alkali and water and then a mineral acid or a mixture of a mineral acid with at least one diluent selected from water, dimethyl sulfoxide and a monohydric alcohol having 1 to 3 carbon atoms is incorporated into the so-formed solution, thereby neutralizing the caustic alkali present in the solution to precipitate a finely divided gamma phase quinacridone.

9 Claims, No Drawings

PROCESS FOR PREPARING GAMMA PHASE QUINACRIDONE

BACKGROUND OF THE INVENTION

1. Field of the Invention

This invention relates to a process for preparing a finely divided gamma crystal phase quinacridone from a crude quinacridone of an arbitrary crystal phase.

2. Description of the Prior Art

It is well known that quinacridone expressed by the following structural formula (I) possesses three crystal modifications, i.e., alpha, beta and gamma crystal phases.

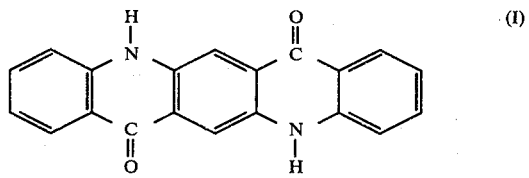

(I)

Of the three crystal phases, a gamma crystal phase exhibits an attractive bright shade as well as a high degree of fastness, i.e., resistance to change under various conditions, such as heat, weather, chemicals and solvents, as compared with the alpha and beta crystal phase quinacridones. Therefore, a gamma crystal phase quinacridone is of a wide use.

Many proposals have heretofore been made for the preparation of a gamma crystal phase quinacridone, some examples being the following.

(i) A crude quinacridone is subjected to salt-milling by using an inorganic salt, such as sodium hydroxide, thereby reducing the particle size thereof and subsequently, the salt-milled quinacridone is treated with dimethylformamide (British Pat. No. 828,052).

(ii) A crude quinacridone of an arbitrary crystal phase is ground by using, for example, a ball mill, and then, the finely divided crude quinacridone is heated in a hydrous or anhydrous state, at a temperature of from 80° to 200° C., in the presence of an organic solvent having a solubility of at least 5% by weight in water (Japanese Patent Publication No. 9,272/1964).

(iii) A crude quinacridone is heated together with methanol and potassium hydroxide (Japanese Patent Publication No. 20,073/1964).

(iv) An alpha crystal phase quinacridone is mixed with dimethyl sulfoxide in the presence or absence of boric acid, and the mixture is boiled (Japanese Patent Publication No. 6,098/1965).

(v) An alpha crystal phase quinacridone is heated together with an aliphatic polyamine ($NH_2(R.NH)_nH$, n=2 or 3) (Japanese Patent Publication No. 1,704/1969).

(vi) An alpha crystal phase quinacridone is heated in alpha-pyrrolidone (British Pat. No. 1,080,394).

(vii) A crude quinacridone is dissolved in a concentrated sulfuric acid and, subsequently, added drop by drop into a lower alcohol, such as methanol, to thereby precipitate a gamma crystal phase quinacridone (British Pat. No. 1,110,997).

The above mentioned conventional processes are not completely satisfactory for the following reasons. The process recited in item (i) requires the step of drying a crude quinacridone prior to the salt-milling thereof. A substantial period of time is needed for the salt-milling and the treatment with dimethylformamide. Moreover, this process recited in item (i) requires the step of washing the quinacridone precipitate for the removal of the inorganic salt therefrom. Thus, a substantial period of time is needed for the completion of the entire process of item (i), and complicated operations are also necessary. In the processes recited in items (ii) through (vi), the resulting quinacridone product particles are not sufficiently minute for use in pigment, and hence, a step of comminuting the product particles or the raw material particles is necessary. The process recited in item (vii) involves the risk that quinacridone will be undesirably sulfonated, and thus, the permmissible operating conditions for dissolution and reprecipitation are particularly restricted. Furthermore, the product particles obtained by the process of item (ii) are generally poor in thermal resistance and weather resistance.

Moreover, all of the conventional processes have a defect such that, in the case where crude qunacridone contains impurities in its particles, it is difficult to remove the purities in the course of manufacturing gamma crystal phase quinacridone. Therefore, it is generally required to purify crude quinacridone prior to the use thereof in the manufacture of the gamma crystal phase quinacridone.

SUMMARY OF THE INVENTION

It now has been found that crude quinacridone is capable of being completely dissolved in dimethyl sulfoxide in the presence of a caustic alkali and water to form a bluish purple solution; that the so formed solution is capable of being strained or filtered by using, for example, a No. 4 glass filter, thereby to remove foreign matters and impurities; that the above-mentioned solution retains its solution form without precipitation of quinacridone crystals, even when the solution is cooled to room temperature or a lower temperature, and; further, that particle size of a finely divided gamma crystal phase quinacridone, which is quantitatively precipitated from the above-mentioned solution by neutralizing the solution with a mineral acid such as sulfuric acid, not diluted or diluted with a diluent, such as water, dimethyl sulfoxide or a lower monohydric alcohol, can be arbitrarily controlled depending upon the amount of dimethyl sulfoxide used and the neutralization temperature.

It is, therefore, a main object of the present invention to provide a novel process for producing finely divided gamma crystal quinacridone pigments, the particle size of which can be arbitrarily controlled, and from which foreign matters and impurities can be easily removed during the production process.

In accordance with the process of the present invention the finely divided gamma crystal phase quinacridone pigments are prepared by the steps of: dissolving a crude quinacridone, which may be of an arbitrary crystal phase, in dimethyl sulfoxide in the presence of a caustic alkali and water, and; then, incorporating in the solution, so formed, a mineral acid or a mixture of a mineral acid with at least one diluent selected from water, dimethyl sulfoxide and a lower monlhydric alcohol, thereby neutralizing the caustic alkali present in the solution to precipitate the finely divided gamma crystal phase quinacridone.

DESCRIPTION OF THE PREFERRED EMBODIMENTS

The crude quinacridone used as the starting material may be of an arbitrary crystal phase and of any particle size. The crude quinacridone may be either in the form of a dry particle or a wet cake. However, the wet cake should preferably be dehydrated as much as possible, and usually to a moisture content of less than approximately 300% by weight, based on the weight of the dried cake.

Dimethyl sulfoxide used as solvent may not be completely anhydrous, and may contain a minor amount, usually approximately 10% by weight or less, of water. In corporation of such an amount of water is convenient for preventing the solvent from freezing in winter. The amount of dimethyl sulfoxide is usually within the range of from 4 to 20 times by weight of the amount of the crude quinacridone. By varying the proportion of dimethyl sulfoxide to crude quinacridone, the particle size of the resulting quinacridone pigments can be arbitrarily controlled. The smaller the proportion of dimethyl sulfoxide to crude quinacridone, the smaller the particle size of the resulting pigments.

The caustic alkali (i.e., alkali metal hydroxide) used includes, for example, sodium hydroxide, potassium hydroxide and lithium hydroxide. These caustic alkalis may be used alone or in combination. Of these, potassium hydroxide is preferable. The amount of the caustic alkali is usually at least 1.5 moles, preferably in the range of from 2 to 2.5 moles, per mole of crude quinacridone.

The caustic alkali may be used in the form of either a finely divided powder or an aqueous solution. However, the caustic alkali should preferably be used in the form of an aqueous solution for the convenience in the dissolution operation, i.e., so as to readily and rapidly dissolve crude quinacridone therein. In the case where an aqueous caustic alkali solution is used, consideration should preferably be given to the fact that the amount of water does not exceed 30% by weight, based on the weight of dimethyl sulfoxide. When the amount of water exceeds approximately 30% by weight, based on the weight of dimethyl sulfoxide, the dissolving power becomes poor, and hence, for complete dissolution it is necessary to raise the proportion of dimethyl sulfoxide to crude quinacridone to more than approximately 20:1 by weight, thereby leading to a reduction in the purification efficiency of quinacridone.

The dissolution of crude quinacridone in the dimethyl sulfoxide-aqueous caustic alkali solution is preferably effected at an elevated temperature. In order to avoid the decomposition of dimethyl sulfoxide and the reflux of water inside the reactor, the crude quinacridone-solvent mixture should preferably be maintained at a temperature of from 60° to 90° C. for a period of from 0.5 to 6 hours, particularly 1 to 3 hours, while being stirred. If the crude quinacridone-solvent mixture is maintained under such conditions in an air atmosphere, quinacridone will be undesirably subject to oxidation in the presence of alkali thereby to be gradually converted to quinacridone-quinone. In order to avoid this undesirable oxidation, the dissolution of crude quinacridone should preferably be effected in a non-oxidizing gas atmosphere, such as nitrogen.

The solution of quinacridone in dimethyl sulfoxide, so formed, maintains its solution form without precipitation of crystals, even when the solution is cooled to room temperature or lower. Accordingly, foreign matter or impurities present in the solution can easily be removed therefrom by filtration using, for example, a 4-G glass filter.

The alkaline solution of quinacridone in dimethyl sulfoxide is then neutralized with a non-diluted or diluted mineral acid thereby to precipitate quinacridone particles. As the mineral acid sulfuric acid is preferably used. The diluent used is selected from water, dimethyl sulfoxide and a monohydric alchol having 1 to 3 carbon atoms, such as methyl alcohol, ethyl alcohol and propyl alcohol. These diluents many be used either alone or in combination. The amount of the diluent used is preferably such that the diluted mineral acid contains at least approximately 30% by weight of the mineral acid in the case of water and/or dimethyl sulfoxide, and at least approximately 1% by weight of the mineral acid in the case of the lower monohydric alcohol. The amount of the non-diluted or diluted mineral acid is preferably such that its proportion to the dimethyl sulfoxide used as the solvent is within the range of from 4:1 to 20:1 by weight, more preferably from 5:1 to 10:1 by weight.

The particle size of quinacridone to be precipitated can be controlled by adjusting the temperature at which the alkaline solution of quinacridone in dimethyl sulfoxide is neutralized. In general, the lower the neutralizing temperature, the smaller the particle size. For example, the average particle size is one micron at a neutralizing temperature of 60° C., 0.5 micron at 45° to 50° C., from 0.2 to 0.3 micron at 30° to 35° C., and from 0.1 to 0.2 micron at 10° to 20° C. When the neutralizing temperature is lower than approximately 20° C., the particle size is changed only to a negligible extent depending upon the temperature change. Thus, the neutralizing temperature may suitably be determined depending upon the desired average particle size of quinacridone pigments, usually within the range of from 10° to 80° C.

The quinacridone precipitate obtained by neutralization may be filtered, washed, and then, surface-treated by a conventional procedure, thereby to obtain finely divided gamma crystal phase quinacridone pigments exhibiting a high strength and an attractive bright shade, as well as high heat- and light- resistance. The gamma crystal phase can be identified by the fact that, when the resulting quinacridone pigments are analyzed by X-ray diffractiometry, they exhibit powerful peaks at a $2\theta$ of 6.4°, 13.7° and 26.3°, and weak peaks at a $2\theta$ of 16.8°, 20.2° and 23.6°, respectively.

The advantages of the process of the present invention over conventional processes for preparing gamma crystal phase quinacridone pigments are summarized as follows.

(a) Since crude quinacridone is capable of being completely dissolved in dimethyl sulfoxide in the presence of a caustic alkali and water, foreign matter and impurities can easily and completely be removed by filtering the solution, and directly after the removal of foreign matter and impurities, the solution can be subjected to precipitation. Furthermore, the operations of filtration and precipitation are simple.

(b) The intended finely divided gamma crystal phase can be obtained independently of the particular crystal phase of crude quinacridone and the particular particle size thereof.

(c) The dissolution of crude quinacridone can be effected without employing high temperature and pressure and within a short period of time.

(d) The particle size of quinacridone to be precipitated can be arbitrarily controlled by varying the proportion of quinacridone to dimethyl sulfoxide and the temperature at which the alkaline solution of quinacridone in dimethyl sulfoxide is neutralized for precipitation.

(e) A substantial period of time is not required for the entire process of the invention and the apparatus used is not complicated.

The invention will be further illustrated by the following examples.

EXAMPLE 1

Twenty grams of a crude quinacridone having a particle size of at least 10 microns and 200 grams of dimethyl sulfoxide (commercially available first grade quality) were placed in a flask, and subsequently, an aqueous solution of 10 grams of potassium hydroxide in 10 milliliters of water was added to the charge while the charge was stirred in a nitrogen atmosphere. The resultant mixture was maintained at a temperature of from 70° to 80° C. for a period of 1.5 hours, while being stirred, on a hot water bath, thereby to obtain a bluish purple solution. The solution was cooled to room temperature and, then, filtered by suction by using a 4-G glass filter, to remove therefrom trace amounts of foreign matter. An aqueous solution of 9.5 grams of concentrated sulfuric acid in 10 milliliters of water was added drop by drop to the filtered solution, while the filtered solution was maintained at a temperature of 20° C. and was thoroughly stirred. As neutralization proceeded due to this addition of sulfuric acid, the initial bluish purple solution gradually increased its viscosity, and at the time that approximately two thirds of the entire amount of sulfuric acid to be added was added thereto, its viscosity reached the maximum value, and concurrently, its color changed to red. After the addition of the entire amount of sulfuric acid was completed, stirring of the red colored slurry continued for a period of 30 minutes, and subsequently, the slurry was filtered by suction, by using a 4-G glass filter. The red suction cake so obtained after hydro-extraction was placed in one liter of water, maintained at a temperature of 90° C., and stirred for a period of 60 minutes, to be thereby dispersed therein. The aqueous dispersion was filtered again to obtain a cake in a manner similar to that described above. The dispersing of the cake in water and the filtration of the aqueous dispersion were repeated until a colorless filtrate was obtained. The resultant cake was dried at a temperature of 60° C. for a period of 24 hours by using a hot air dryer. A finely divided red powder was obtained at an approximately quantitative yield.

The finely divided red powder was proved by an X-ray diffraction analysis to be a gamma crystal phase quinacridone, because the powder exhibited powerful peaks at a $2\theta$ of 6.4°, 13.7° and 26.3°, and weak peaks at a $2\theta$ of 16.8°, 20.2° and 23.6°, respectively. The finely divided red powder was further proved by an electron microscopic photograph (transmission type, 20,000 magnification) to possess a substantially uniform particle size of approximately 0.2 micron. The powder was proved by a painting test to exhibit good tinctorial strength, bright shade and good toning.

When the finely divided red powder was subjected to a light exposure test using a carbon arc, the powder exhibited little or no change in color at an exposure time of 150 hours. In contrast, a conventional gamma crystal phase quinacridone pigment, which was prepared by grinding a crude quinacridone by using a ball mill, followed by boiling-treating the ground quinacridone in a methanol-potassium hydroxide mixture, exhibited a significant deterioration at an exposure time of 150 hours.

EXAMPLE 2

Following the procedure mentioned in Example 1, a finely divided gamma crystal phase quinacridone was prepared from a crude quinacridone, wherein the neutrarization of the solution of the crude quinacridone in dimethyl sulfoxide was effected while the solution was maintained at a temperature of 150° C., with all other conditions remaining substantially the same.

A finely divided bright red powder was obtained at an approximately quantitative yield. This powder was proved by an electromicroscopic photograph (transmission type, 20,000 magnification) to possess a substantially uniform particle size falling within the narrow range of from 1.0 to 1.2 microns.

EXAMPLE 3

A hundred grams of a crude quinacridone similar to that used in Example 1 and 500 grams of dimethyl sulfoxide were placed in a separable flask, and subsequently, an aqueous solution of 50 grams of potassium hydroxide in 100 milliliters of water was added to the charge, while the charge was stirred in a nitrogen atmosphere. The resultant mixture was maintained at a temperature of from 70° to 80° C. for a period of 120 minutes, while being stirred on a hot water bath. After the solution so obtained was cooled to room temperature, the solution was filtered by suction by using a 4-G glass filter. A solution of 47 grams of concentrated sulfuric acid in 50 milliliters of dimethyl sulfoxide was added to the filtered solution, while the filtered solution was maintained at a temperature of from 15° to 20° C. and thoroughly stirred. The red colored slurry so formed was filtered; and the obtained cake was repeatedly washed and, finally, dried, in a manner similar to that mentioned in Example 1. A finely divided bright bluish red powder was obtained at an approximately quantitative yield. This powder was proved by an electromicroscopic photograph (transmission type, 20,000 magnification) to possess a substantially uniform particle size of a narrow range of from 0.1 to 0.2 micron. The powder was further proved by an X-ray diffraction analysis to be a gamma crystal phase quinacridone exhibiting good tinctorial strength.

EXAMPLE 4

Twentty grams (0.064 mole) of a crude quinacridone and 200 grams of dimethyl sulfoxide (commercially available first grade quality) were placed in a four neck flask, and subsequently, an aqueous solution of 5.13 grams (0.128 mole) of sodium hydroxide in 10 milliliters of water was added to the charge, while the charge was stirred in a nitrogen atmosphere. The resultant mixture was maintained at a temperature of from 80° to 90° C. for a period of 60 minutes, while being stirred on a hot water bath. After the solution so obtained was cooled to room temperature, the solution was filtered by suction by using a 4-G glass filter. Only a negligible amount of foreign matter remained on the filter, which fact showed that the quinacridone was in a completely dissolved form. An aqueous solution of 7 grams (0.071 mole) of concentrated sulfuric acid in 10 milliliters of water was added to the filtered solution, while the filtered solution was maintained at a temperature of 20° C. and thoroughly stirred. The red colored slurry so formed was filtered, and the obtained cake was repeatedly washed and, finally, dried, in a manner similar to that mentioned in Example 1. A finely divided red powder was obtained at an approximately quantitative yield. This powder had a substantially uniform particle size of a narrow range of from 0.1 to 0.2 micron. This powder was proved by an X-ray diffraction analysis to be a gamma crystal phase quinacridone.

EXAMPLE 5

Twenty grams of a crude quinacridone having a particle size of approximately 10 microns and 200 grams of commercially available dimethyl sulfoxide were placed in a 300 milliliter volume separable flask, and subsequently, the charge was thoroughly stirred at room temperature in a nitrogen atmosphere. Then, an aqueous solution of 10 grams of potassium hydroxide in 10 milliliters of water was added to the charge, and then, the mixture was stirred at a temperature of from 70° to 80° C. for a period of 1.5 hours, in a nitrogen atmosphere, on a hot water bath, thereby to obtain a bluish purple solution. The warm bluish purple solution was filtered by suction by using a glass filter to remove therefrom trace amounts of foreign matter. After the filtered solution was cooled to room temperature, the solution was added drop by drop through a dropping funnel to 250 milliliters of cold methanol containing 10 grams of sulfuric acid. During this neutralization process, the reaction mixture was maintained at a temperature of 20° C. by cooling the exothermic reaction mixture by cold water and by controlling the rate of addition of the filtered solution. After the addition of the filtered solution was completed, the stirring of the neutralized slurry continued, at room temperature, for a period of 30 minutes, and subsequently, the slurry was filtered by using a glass filter. The slightly bluish bright red cake so obtained was again placed in the flask, wherein the cake was washed with one liter of hot water of 90° C., for a period of 60 minutes, and thereafter, filtered. This washing-filtration was repeated twice, and finally, the resultant cake was dried at a temperature of 60° C., for a period of 24 hours, by using a hot air dryer, thereby to obtain a finely divided slightly bluish bright red powder at a yield of 19.9 grams.

The finely divided red powder exhibited an X-ray diffraction pattern corresponding to a gamma crystal phase quinacridone, i.e., exhibited powerful peaks at a $2\theta$ of 6.4°, 13.7° and 26.3°, and weak peaks at a $2\theta$ of 16.8°, 20.2° and 23.6°, respectively. This powder was proved by an electromicroscopic photograph (transmission type, 20,000 magnification) to possess a substantially uniform particle size falling within the range of from 0.1 to 0.3 micron. The powder was proved by a painting test to exhibit good tinctorial strength and bright shade. When the powder was subjected to a light exposure test using a carbon arc, the powder exhibited little or no change in color at an exposure time of 150 hours. In contrast, a conventional gamma crystal phase quinacridone pigment, which was prepared by dissolving a crude quinacridone, similar to that used in this Example, in concentric sulfuric acid, followed by adding the obtained solution drop by drop to cold methanol, exhibited a significant deterioration at an exposure time of 150 hours.

EXAMPLE 6

Following the procedure mentioned in Example 5, a finely divided gamma crystal phase quinacridone was prepared from an 1:1 (by weight) crude quinacridone mixture, comprised of a coarse alpha crystal phase particle and a coarse beta crystal phase particle, with all other conditions remaining substantially the same. A finely divided bright red powder was obtained at an approximately quentitative yield. This powder exhibited the same pigmentary proerties as those of the powder obtained in Example 5.

EXAMPLE 7

Following the procedure mentioned in Example 5, a finely divided gamma crystal phase quinacridone was prepared, wherein 7.2 grams of sodium hydroxide were used instead of 10 grams of patassium hydroxide, with all other conditions remaining substnatially the same. A finely divided bright red powder was obtained at an approximately quantitative yield. This powder exhibited an X-ray diffraction pattern corresponding to a gamma crystal phase quinacridone, and pigmentary properties similar to those of the powder obtained in Example 5.

EXAMPLE 8

Fifty grams of a crude quinacridone, 25 grams of potassium hydroxide and 50 milliliters of water were incorporated into 200 milliliters of dimethyl sulfoxide, and dissolved in the dimethyl sulfoxide in a manner similar to that mentioned in Example 5. After the bluish purple solution so obtained was filtered by using a glass filter, there by to remove therefrom trace amounts of foreign matter, the solution was cooled to a temperature of 10° C. The cooled solution was added drop by drop to a mixture of 500 milliliters of ethanol and 25 grams of sulfuric acid, maintained at a temperature of 10° C. on an ice bath, while the reaction mixture was maintained at a temperature of 10° C. under stirring. After the addition of the cooled solution was completed, stirring of the strongly bluish red slurry so formed was continued for a period of 30 minutes. Subsequently, the slurry was filtered, and then, the resultant cake was dispersed in one liter of cold ethanol and again filtered. The cake so obtained was dispersed in one liter of hot water of 90° C. and then filtered. This dispersion-filtration was repeated once and, finally, the cake was dried in hot air at a temperature of 60° C. A finely divided strongly bluish red powder was obtained at an approximately quantitative yield. This powder exhibited an X-ray diffraction pattern corresponding to a gamma crystal phase quinacridone, and pigmentary properties similar to those of the powder obtained in Example 5.

What we claim is:

1. A process for preparing a gamma phase quinacridone from a crude quinacridone of an arbitrary crystal phase, which comprises the steps of:
    dissolving the crude quinacridone in dimethyl sulfoxide in the presence of a caustic alkali and water, and; then
    incorporating in the solution, so formed, sulfuric acid or a mixture of sulfuric acid with a diluent selected from water, dimethyl sulfoxide and a monohydric alcohol having 1 to 3 carbon atoms at a temperature of from 10° to 80° C., thereby neutralizing the cuastic alkali present in the solution to precipitate a finely divided gamma phase quinacridone.

2. A process according to claim 1 wherein the caustic alkali is at least one compound selected from the group consisting of potassium hydroxide and sodium hydroxide.

3. A process according to claim 1 wherein the amount of the caustic alkali is within the range of from 1.5 to 2.5 moles per mole of the crude quinacridone.

4. A process according to claim 1 wherein the amount of dimethyl sulfoxide is within the range of from 4 to 20 times the weight of the crude quinacridone.

5. A process according to claim 1 wherein the amount of water is within the range of from 2.5% to 30% by weight, based on the weight of dimethyl sulfoxide.

6. A process according to claim 1 wherein said mixture is a solution containing at least 30% by weight, based on the weight of the solution, of sulfuric acid diluted with at least one diluent selected from the group consisting of water and dimethyl sulfoxide.

7. A process according to claim 1 wherein said mixtures is a solution containing at least 1.0% by weight, based on the weight of the solution, of sulfuric acid diluted with the monohydric alcohol.

8. A process according to claim 1 or 7 wherein the monohydric alcohol is at least one alcohol selected from the group consisting of methyl alcohol, ethyl alcohol and propyl alcohol.

9. The process of claim 1 wherein the crude quinacridone is dissolved in the dimethyl sulfoxide at a temperature of 70° to 80° C.

* * * * *